United States Patent
Shin et al.

(10) Patent No.: US 10,800,737 B2
(45) Date of Patent: Oct. 13, 2020

(54) METHOD FOR PREPARING TREPROSTINIL AND INTERMEDIATE THEREFOR

(71) Applicant: YONSUNG FINE CHEMICAL CO., LTD., Hwaseong-si, Gyeonggi-do (KR)

(72) Inventors: Hyun Ik Shin, Yongin-si (KR); Hyoseon Lee, Bucheon-si (KR); Kyung Jin Lee, Suwon-si (KR); Kee Young Lee, Seoul (KR); Changyoung Oh, Seongnam-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/096,766

(22) PCT Filed: Apr. 18, 2017

(86) PCT No.: PCT/KR2017/004131
§ 371 (c)(1),
(2) Date: Oct. 26, 2018

(87) PCT Pub. No.: WO2017/188644
PCT Pub. Date: Nov. 2, 2017

(65) Prior Publication Data
US 2019/0119205 A1 Apr. 25, 2019

(30) Foreign Application Priority Data

Apr. 28, 2016 (KR) .................. 10-2016-0052378

(51) Int. Cl.
*C07C 35/37* (2006.01)
*C07C 405/00* (2006.01)
*C07D 317/44* (2006.01)
*C07C 59/72* (2006.01)
*C07B 51/00* (2006.01)

(52) U.S. Cl.
CPC ........ *C07C 405/0083* (2013.01); *C07C 35/37* (2013.01); *C07D 317/44* (2013.01); *C07B 51/00* (2013.01); *C07C 59/72* (2013.01); *C07C 2603/14* (2017.05); *Y02P 20/55* (2015.11)

(58) Field of Classification Search
CPC .............................. C07C 29/56; C07C 29/62
USPC ........................................................ 562/499
See application file for complete search history.

(56) References Cited

U.S. PATENT DOCUMENTS

| 4,306,075 A | 12/1981 | Aristoff |
| 4,306,076 A | 12/1981 | Nelson |
| 2013/0053581 A1 | 2/2013 | Wei et al. |

FOREIGN PATENT DOCUMENTS

| CN | 101891596 A | 11/2010 |
| EP | 2 581 361 A1 | 4/2013 |
| JP | 2-167248 | 6/1990 |
| JP | 2004-526802 | 9/2004 |
| JP | 2013-47224 | 3/2013 |
| KR | 10-2013-00022389 A | 3/2013 |
| WO | 2014/203278 A2 | 12/2014 |
| WO | 2015/073314 A1 | 5/2015 |
| WO | 2016/055819 A1 | 4/2016 |

OTHER PUBLICATIONS

Robert M. Moriarty et al., "The Intramolecular Asymmetric Pauson-Khand Cyclization as a Novel and General Stereoselective Route to Benzindene Prostacyclins: Synthesis of UT-15 (Treprostinil)", J. Org. Chem, 2004, 1890-1902 (13 pages), vol. 69.
International Search Report for PCT/KR2017/004131 dated Nov. 27, 2017.

*Primary Examiner* — Ana Z Muresan
(74) *Attorney, Agent, or Firm* — Sughrue Mion, PLLC

(57) ABSTRACT

The present invention relates to a cost-effective and efficient method for preparing treprostinil with high purity, and an intermediate therefor.

8 Claims, No Drawings

METHOD FOR PREPARING TREPROSTINIL AND INTERMEDIATE THEREFOR

TECHNICAL FIELD

The present invention relates to a method for preparing treprostinil and an intermediate therefor. More particularly, the present invention relates to a cost-effective and efficient method for preparing treprostinil with high purity, and an intermediate therefor.

BACKGROUND ART

Treprostinil represented by the following formula I, 2-((1R,2R,3aS,9aS)-2-hydroxy-1-((S)-3-hydroxyoctyl)-2,3,3a,4,9,9a-hexahydro-1H-cyclopenta[b]naphthalen-5-yloxy) acetic acid, is an active ingredient of Remodulin™, Tyvaso™, and Orenitram™.

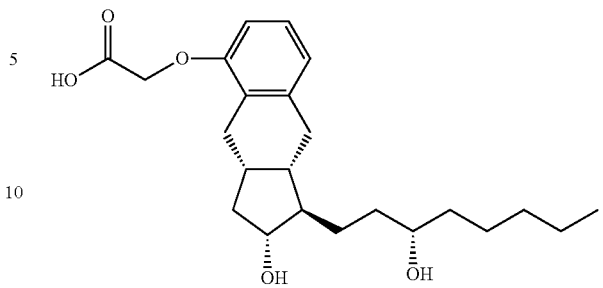

U.S. Pat. No. 4,306,075 discloses a method for preparing treprostinil using an intramolecular alkylation as shown in the following Reaction Scheme 1.

[Reaction Scheme 1]

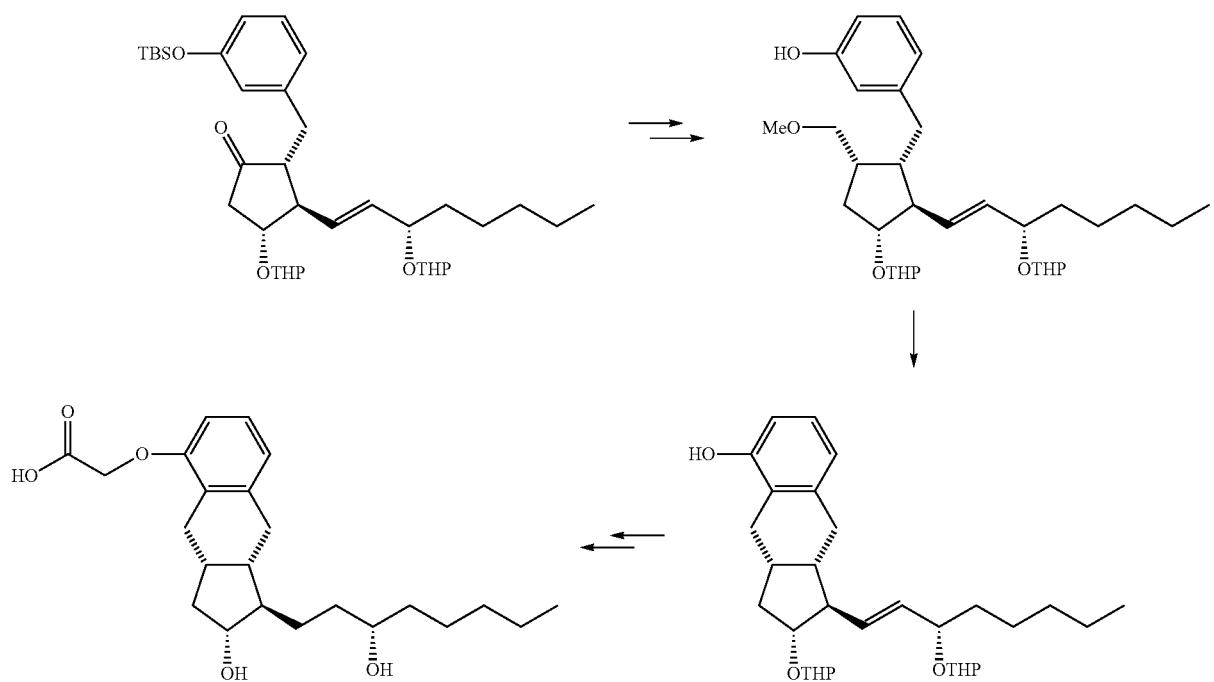

Also, Moriarty, et al., *J. Org. Chem.* 2004, 69, 1890-1902 describes a method for preparing treprostinil using an Pauson-Khand cyclization as a key reaction, as shown in the following Reaction Scheme 2.

[Reaction Scheme 2]

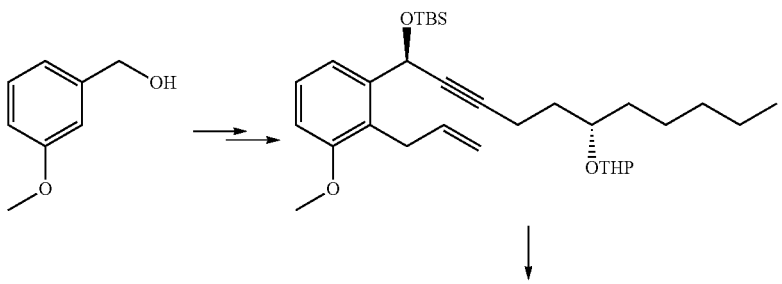

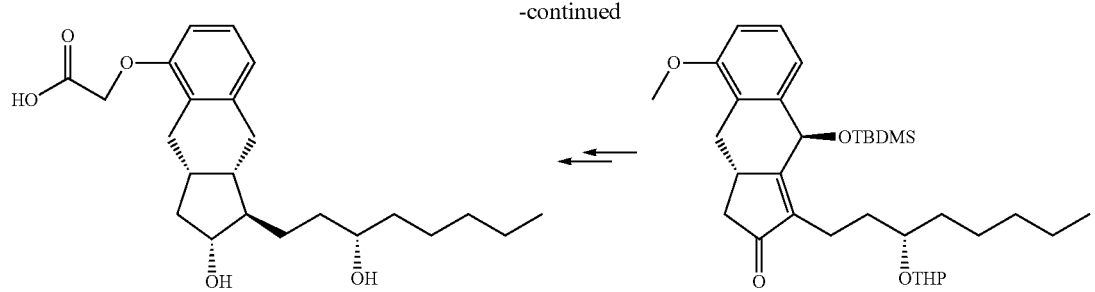

However, the prior preparation methods comprise a large number of steps and column purifications, and thus they have low yields and are unsuitable for mass production.

DISCLOSURE

Technical Problem

An object of the present invention is to provide a cost-effective and efficient method for preparing treprostinil with high purity.

Another object of the present invention is to provide an intermediate used in the above preparation method.

Technical Solution

One embodiment of the present invention relates to a method for preparing a compound of the following formula (1), which comprises the steps of:

(i) converting an alkyl halide or alkenyl tin of the following formula (3) to its cuprate, and subjecting the cuprate to stereoselective 1,4-addition to an α, β-unsaturated ketone of the following formula (2) to obtain a compound of the following formula (4):

(ii) subjecting a ketone group of the compound of the following formula (4) to methenylation to obtain a compound of the following formula (5);

(iii) deprotecting a diol protecting group of the compound of the following formula (5) to obtain a compound of the following formula (6);

(iv) converting a diol of the compound of the following formula (6) to a cyclic carbonate to obtain a compound of the following formula (7);

(v) deprotecting a phenol protecting group of the compound of the following formula (7) to obtain a compound of the following formula (8);

(vi) subjecting the compound of the following formula (8) to intramolecular Friedel-Crafts allylic alkylation to obtain a compound of the following formula (9):

(vii) subjecting the compound of the following formula (9) to hydrogenation to obtain a compound of the following formula (10):

(viii) subjecting the compound of the following formula (10) to alkylation with a compound of the following formula (11) to obtain a compound of the following formula (12); and (ix) hydrolyzing an ester group of the compound of the following formula (12):

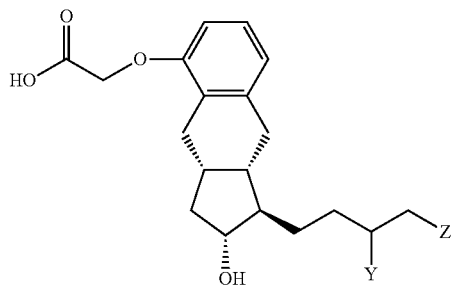

(1)

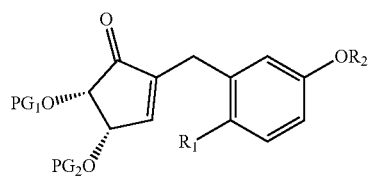

(2)

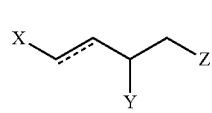

(3)

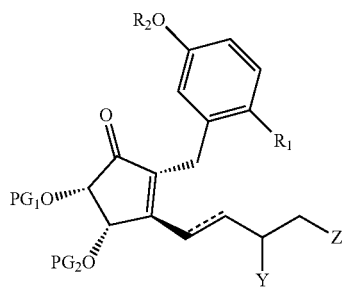

(4)

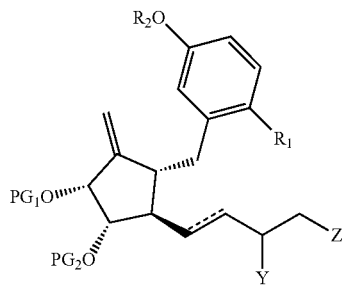

(5)

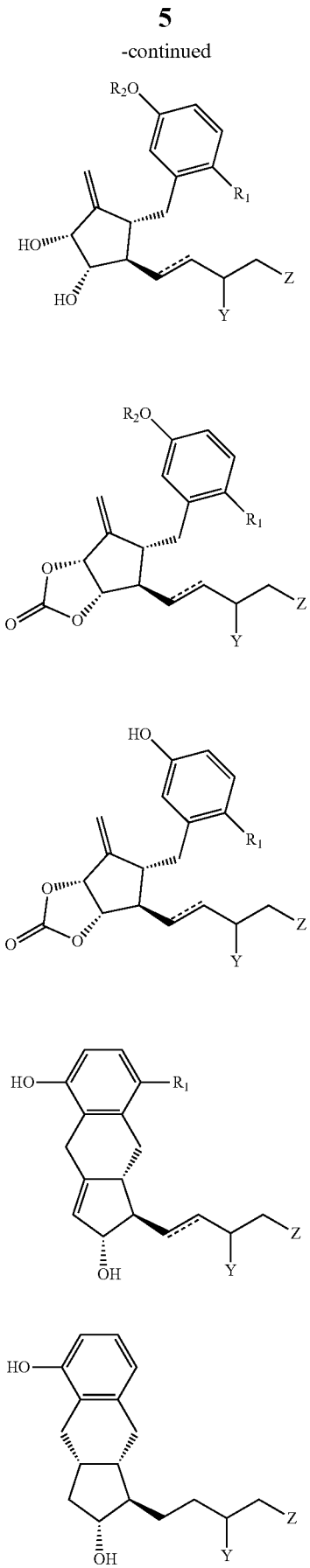

wherein,

⸺ represents a single or double bond between carbon atoms.

$R_1$ represents hydrogen or halogen, $R_2$ represents hydrogen or a hydroxyl protecting group, $R_3$ represents a $C_1$-$C_6$ alkyl group, $PG_1$ and $PG_2$ represent a hydroxyl protecting group each independently or in combination, X represents halogen or $Sn(R_4)_3$, $R_4$ represents a $C_1$-$C_6$ alkyl group, Y represents α-$OR_5$:β-H or α-H:β-$OR_5$, $R_5$ represents hydrogen or a hydroxyl protecting group, Z represents a $C_1$-$C_6$ alkyl group, and X' represents halogen.

The term "$C_1$-$C_6$ alkyl group" as used herein means a linear or branched hydrocarbon having 1 to 6 carbon atoms, which includes methyl, ethyl, n-propyl, i-propyl, n-butyl, i-butyl, t-butyl, n-pentyl, n-hexyl and the like, but is not limited thereto.

In one embodiment of the present invention, the hydroxyl protecting group may include tetrahydropyranyl, benzyl, trimethylsilyl, triethylsilyl, t-butyldimethylsilyl (TBS), and t-butyldiphenylsilyl (TBDPS) and the like, but is not limited thereto.

Particularly, the hydroxyl protecting group formed from a combination of PG and $PG_2$ may be an diol protecting group selected from a group consisting of cyclic acetal, di-t-butylsilylene, 1,1,3,3-tetraisopropyldisiloxanylidene, cyclic carbonate, cyclic sulfonate, and cyclic boronate.

The preparation method of the present invention is, hereinafter, described in more detail referring to the following Reaction Scheme 3. The method depicted in the following Reaction Scheme 3 represents merely a typical example, and various changes may be made to reagents and reaction conditions without limitation.

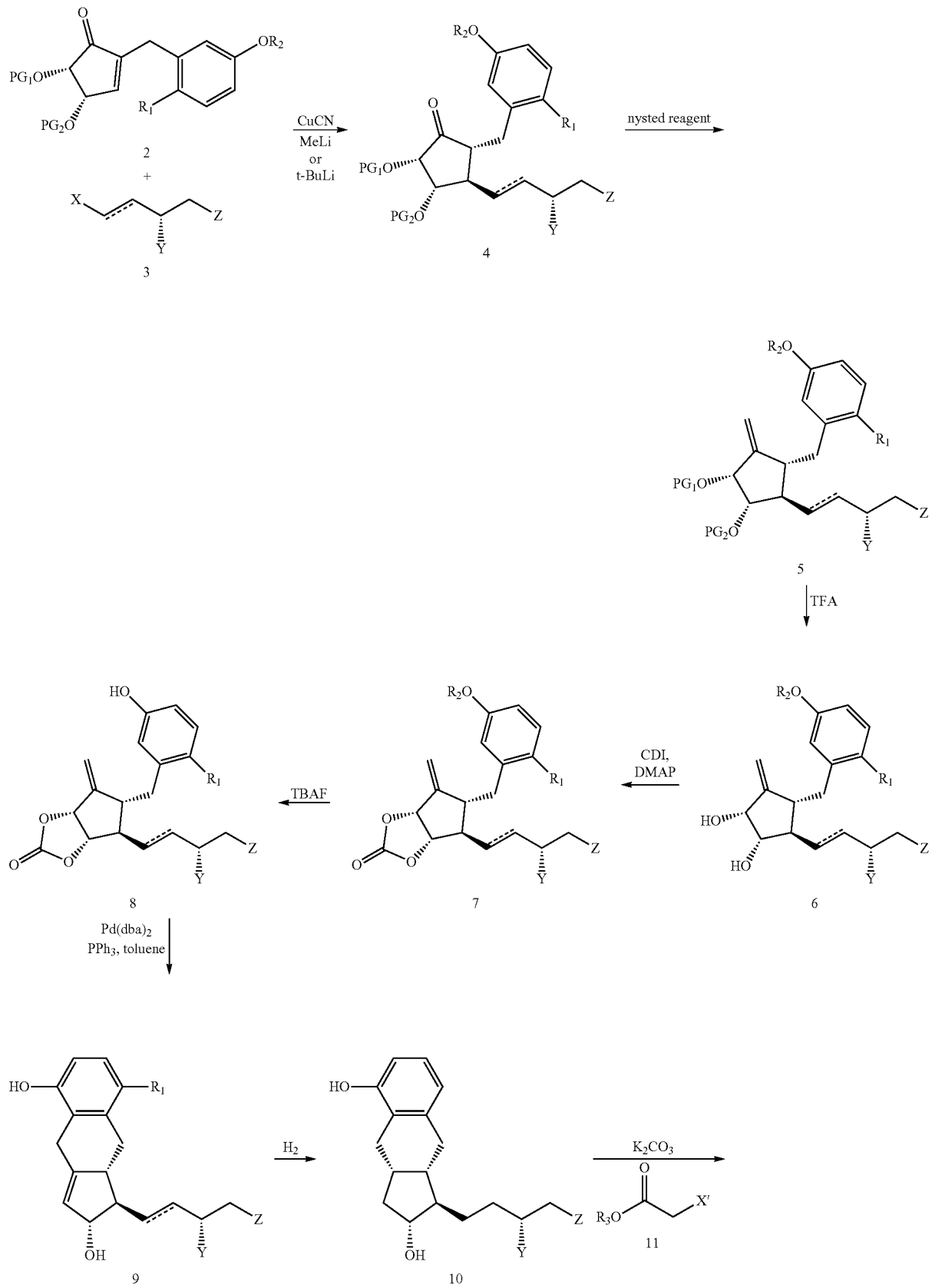

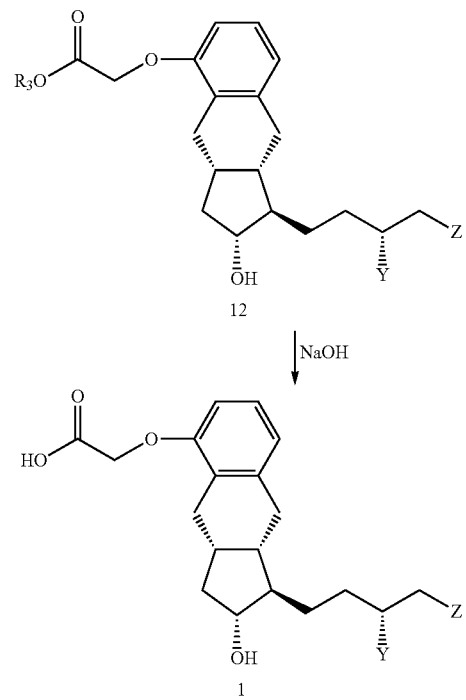

Step 1: Synthesis of Compound of Formula (4)

The compound of formula (4) can be obtained by converting the alkyl halide or alkenyl tin of formula (3) to its cuprate, and subjecting the cuprate to stereoselective 1,4-addition to the α,β-unsaturated ketone of formula (2).

The conversion of the alkyl halide or alkenyl tin of formula (3) to its cuprate may be carried out by adding methyl lithium (MeLi) or t-butyl lithium, and copper cyanide (CuCN).

Then, the 1,4-addition is carried out by adding the α,β-unsaturated ketone of formula (2).

The 1,4-addition is preferably performed at the low temperature of −60° C. or lower.

Step 2: Synthesis of Compound of Formula (5)

The compound of formula (5) can be obtained by subjecting the ketone group of the compound of formula (4) to methenylation.

The methenylation may be carried out, without limitation, by a method known in the art such as Wittig, Tebbe, and Nysted reactions. In particular, a Nysted reagent is preferred.

Step 3: Synthesis of Compound of Formula (6)

The compound of formula (6) can be obtained by deprotecting the diol protecting group of the compound of formula (5).

The deprotection may be carried out under an acidic condition. Particularly, pyridinium p-toluenesulfonate, hydrochloric acid, sulfuric acid, phosphoric acid, acetic acid, or trifluoroacetic acid may be used without limitation, and trifluoroacetic acid is preferred.

In the deprotection, the hydroxyl protecting group of Y may be deprotected as well, if it is a tetrahydropyranyl or silyl group.

Step 4: Synthesis of Compound of Formula (7)

The compound of formula (7) can be obtained by converting the diol of the compound of formula (6) to a cyclic carbonate.

The conversion may be carried out, without limitation, using urea, 1,1-carbonyldiimidazole (CDI), phosgene, diphosgene, triphosgene and the like. In particular, 1,1-carbonyldiimidazole is preferred.

The conversion may be carried out in the presence or absence of a base. The base may be 4-dimethylaminopyridine (DMAP), triethylamine (TEA), diisopropylethylamine (DIPEA) and the like, but is not limited thereto. Preferably, 4-dimethylaminopyridine may be used.

Step 5: Synthesis of Compound of Formula (8)

The compound of formula (8) can be obtained by deprotecting the phenol protecting group of the compound of formula (7).

The deprotection may be carried out using various fluoride (F) compounds, particularly tetra-n-butylammonium fluoride (TBAF).

Step 6: Synthesis of Compound of Formula (9)

The compound of formula (9) can be obtained by subjecting the compound of formula (8) to intramolecular Friedel-Crafts allylic alkylation.

The intramolecular Friedel-Crafts allylic alkylation may be carried out using a palladium catalyst and a ligand.

Examples of the palladium catalyst may include tetrakis(triphenylphosphine)palladium(0) (Pd(PPh$_3$)$_4$), allylpalladium(II) chloride dimer ([Pd(C$_3$H$_5$)Cl]$_2$), bis(dibenzylideneacetone)palladium(0) (Pd(dba)$_2$), and tris(dibenzylideneacetone)dipalladium(0) (Pd$_2$(dba)$_3$), but are not limited thereto. Particularly, bis(dibenzylideneacetone) palladium(0) or tris(dibenzylideneacetone)dipalladium(O) is preferred.

Examples of the ligand may include triphenylphosphine (PPh$_3$), DACH-phenyl trost ligand, 2,2-bis(diphenylphosphino)-1,1-binaphthalene (BINAP), bis[(2-diphenylphosphino)phenyl]ether (DPEPhos), 4,5-bis(diphenylphosphino)-9,9-dimethylxanthene (Xantphos), tri(o-tolyl) phosphine (P(o-tolyl)$_3$), 1,4-bis(diphenylphosphino)butane (dppb), ethylenebis(diphenylphosphine) (dppe), 1,1'-ferrocenediyl-bis(diphenylphosphine) (dppf), and 1,3-bis(diphenylphosphino)propane (dppp), but are not limited thereto. Particularly, triphenylphosphine is preferred.

As a reaction solvent, toluene, tetrahydrofuran, methanol, diethylether, 1,4-dioxane, acetonitrile, methylenechloride, etc. may be used. Particularly, toluene is preferred.

The reaction is preferably performed at room temperature.

Step 7: Synthesis of Compound of Formula (10)

The compound of formula (10) can be obtained by subjecting the compound of formula (9) to hydrogenation.

The hydrogenation may be carried out using Pd/C under a basic condition.

As the basic condition, sodium hydroxide, potassium hydroxide, potassium carbonate, triethylamine, etc. may be used. Particularly, triethylamine is preferred.

As a reaction solvent, methylenechloride, ethylacetate, methanol, ethanol, etc. may be used. Particularly, methanol is preferred.

In this step, the hydroxyl protecting group of Y may be simultaneously deprotected, if it is a benzyl group.

Step 8: Synthesis of Compound of Formula (12)

The compound of formula (12) can be obtained by subjecting the compound of formula (10) to alkylation with the compound of formula (11).

The alkylation may be carried out in the presence of a base. Examples of the base may include sodium hydride, cesium carbonate, and potassium carbonate. Particularly, potassium carbonate is preferred.

As a reaction solvent, dimethylformamide, acetonitrile, tetrahydrofuran, acetone, etc. may be used. Particularly, acetone is preferred.

Further, the alkylation is preferably performed at the temperature of 50-60° C.

Step 9: Synthesis of Compound of Formula (1)

The compound of formula (1) can be obtained by hydrolyzing the ester group of the compound of formula (12).

The hydrolysis may be carried out in the presence of a base. Examples of the base may include lithium hydroxide, sodium hydroxide, and potassium hydroxide. Particularly, sodium hydroxide is preferred.

As a reaction solvent, methanol, ethanol or propanol, and water may be used. Particularly, ethanol and water are preferred.

One embodiment of the present invention relates to a compound of the following formula (8) which is an intermediate for the preparation of treprostinil:

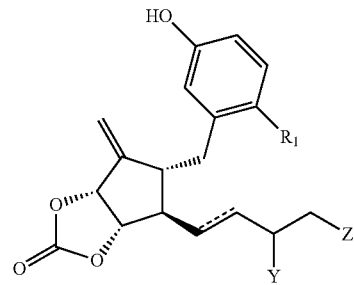

wherein

⁓ represents a single or double bond between carbon atoms, particularly a single bond, R$_1$ represents hydrogen or halogen, particularly chlorine, Y represents α-OR$_5$:β-H or α-H:β-OR$_5$, particularly α-OR$_5$:β-H, R$_5$ represents hydrogen or a hydroxyl protecting group, and Z represents a C$_1$-C$_6$ alkyl group, particularly n-butyl.

One embodiment of the present invention relates to a method for preparing a compound of the following formula (8), which comprises the steps of:

(i) converting an alkyl halide or alkenyl tin of the following formula (3) to its cuprate, and subjecting the cuprate to stereoselective 1,4-addition to an α, β-unsaturated ketone of the following formula (2) to obtain a compound of the following formula (4):

(ii) subjecting a ketone group of the compound of the following formula (4) to methenylation to obtain a compound of the following formula (5);

(iii) deprotecting a diol protecting group of the compound of the following formula (5) to obtain a compound of the following formula (6);

(iv) converting a diol of the compound of the following formula (6) to a cyclic carbonate to obtain a compound of the following formula (7); and (v) deprotecting a phenol protecting group of the compound of the following formula (7):

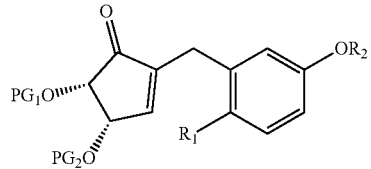

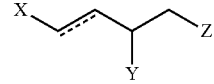

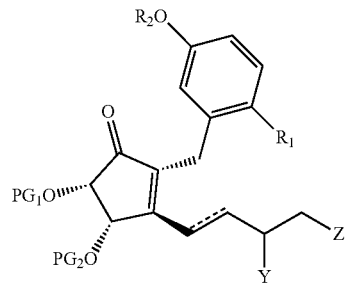

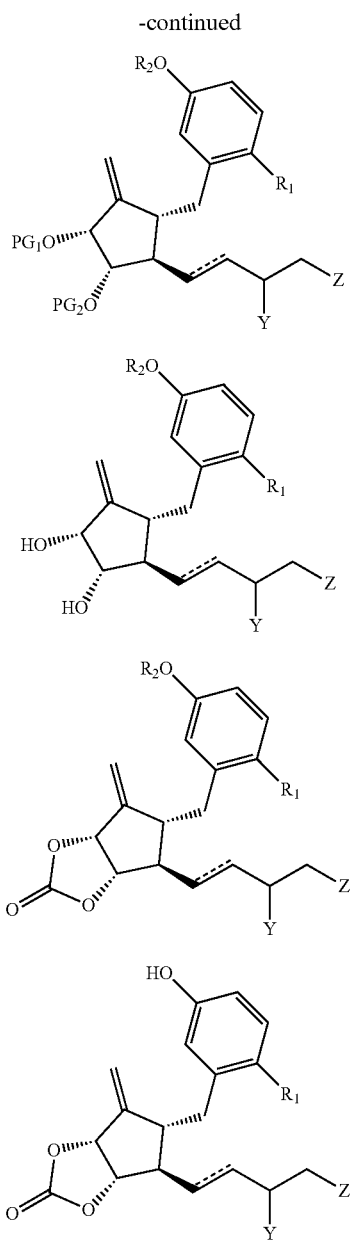

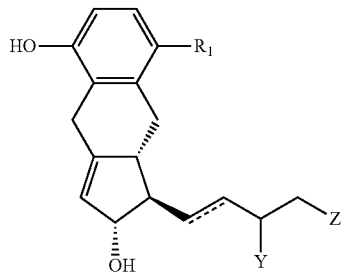

wherein, $\equiv$ represents a single or double bond between carbon atoms, $R_1$ represents hydrogen or halogen, $R_2$ represents hydrogen or a hydroxyl protecting group, $PG_1$ and $PG_2$ represent a hydroxyl protecting group each independently or in combination, X represents halogen or $Sn(R_4)_3$, $R_4$ represents a $C_1$-$C_6$ alkyl group, Y represents $\alpha$-$OR_5$:$\beta$-H or $\alpha$-H:$\beta$-$OR_5$, $R_5$ represents hydrogen or a hydroxyl protecting group, and Z represents a $C_1$-$C_6$ alkyl group.

The method for preparing the compound of formula (8) includes the same steps (i) to (v) as in the above method for preparing treprostinil, and thus a detailed description thereof will be omitted.

One embodiment of the present invention relates to a compound of the following formula (9) which is an intermediate for the preparation of treprostinil:

wherein, $\equiv$ represents a single or double bond between carbon atoms, particularly a single bond, $R_1$ represents hydrogen or halogen, particularly chlorine, Y represents $\alpha$-$OR_5$:$\beta$-H or $\alpha$-H:$\beta$-$OR_5$, particularly $\alpha$-$OR_5$:$\beta$-H, $R_5$ represents hydrogen or a hydroxyl protecting group, and Z represents a $C_1$-$C_6$ alkyl group, particularly n-butyl.

One embodiment of the present invention relates to a method for preparing the compound of formula (9), which comprises a step of subjecting the compound of formula (8) to intramolecular Friedel-Crafts allylic alkylation.

The method for preparing the compound of formula (9) includes the same step (vi) as in the above method for preparing treprostinil, and thus a detailed description thereof will be omitted.

One embodiment of the present invention relates to a method for preparing the compound of formula (10), which comprises a step of subjecting the compound of formula (9) to hydrogenation.

The method for preparing the compound of formula (10) includes the same step (vii) as in the above method for preparing treprostinil, and thus a detailed description thereof will be omitted.

Advantageous Effects

In accordance with the method of the present invention, treprostinil with high purity can be cost-effectively and efficiently prepared by using intramolecular Friedel-Crafts allylic alkylation. Therefore, the method of the present invention can be effectively used for commercial mass production of treprostinil.

BEST MODE

The present invention will be described in more detail by following examples. It will be obvious to those skilled in the art that these examples are merely described for illustration of the present invention and the scope of the present invention is not limited thereto.

Example 1: Synthesis of Compound of Formula (4a)

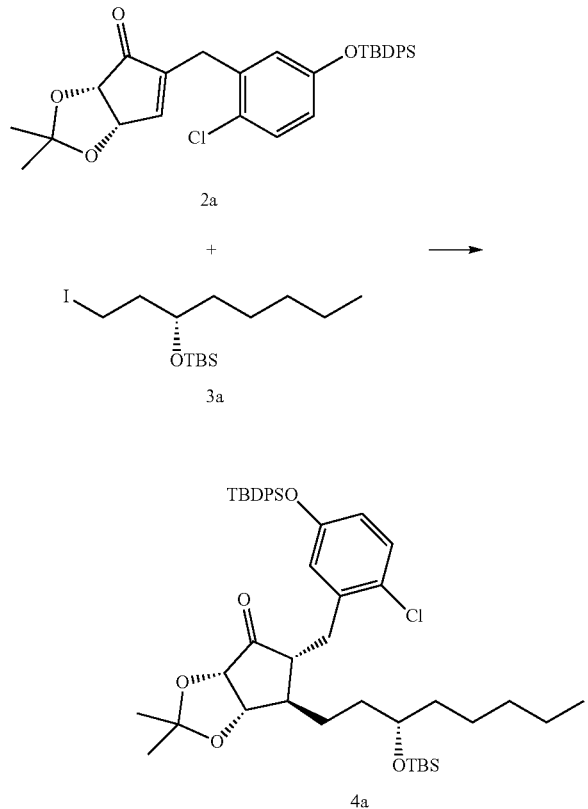

The compound of formula (3a) (15.29 g) was dissolved in diethylether (230 mL), cooled to −68° C., and then stirred for 30 minutes, t-Butyl lithium (45.65 mL) was slowly added dropwise for 20 minutes with maintaining the internal temperature of −60° C., and the resulting solution was stirred for 30 minutes with maintaining the temperature below −65° C. Copper cyanide (1.66 g) was added at the temperature of −60° C. or lower and the resulting solution was warmed to −15° C. to observe complete dissolution, followed by cooling below −65° C. To the resulting solution was slowly added dropwise the compound of formula (2a) (8.21 g) dissolved in diethylether (120 mL) with maintaining the temperature of −60° C. or lower. The resulting solution was stirred for 10 minutes and then warmed to −10° C. A solution (400 mL) mixing saturated ammonium chloride aqueous solution with ammonia water at a ratio of 6:1 was added dropwise thereto, followed by stirring for 30 minutes. When the color of the aqueous layer turned into dark blue, the organic layer was separated, and dried over sodium sulfate, followed by filtration, and concentration of the filtrate under reduced pressure. The resulting residue was subjected to chromatography (ethyl acetate:n-hexane=1:10) to give the compound of formula (4a) (9.52 g, 70.4%).

$^1$H NMR (300 MHz, CDCl$_3$, δ ppm): 7.65-7.69 (m, 4H), 7.34-7.44 (m, 6H), 7.06 (dd, J=6.9 Hz, 1H), 6.65-6.66 (m, 1H), 6.59-6.62 (m, 2H), 5.02-5.05 (m, 1H), 4.43 (d, J=5.4 Hz, 1H), 3.39 (bs, 2H), 1.39 (s, 3H), 1.33 (s, 3H), 1.09 (s, 9H).

Example 2: Synthesis of Compound of Formula (5a)

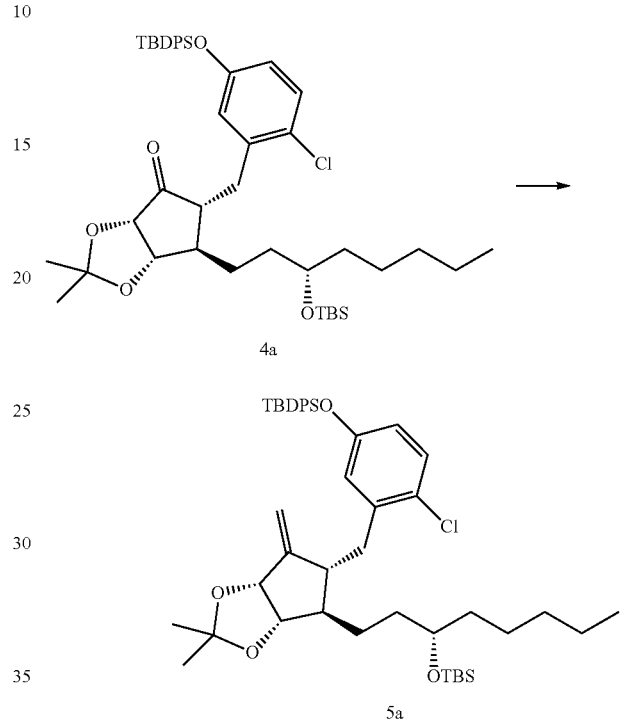

20% Nysted reagent (26.36 mL) was added to THF (120 mL) at room temperature, followed by cooling to −20° C. To the resulting mixture was slowly added dropwise the compound of formula (4a) (8.53 g) dissolved in methylene chloride (60 mL). The resulting solution was cooled to −60° C. or lower, and 1.0M titanium tetrachloride (12 mL) was slowly added dropwise thereto with maintaining the temperature below −60° C. The resulting solution was warmed to room temperature and stirred for 2 hours. Saturated sodium hydrogen carbonate aqueous solution (400 mL) was added thereto. After the resulting solution turned from black into white, the organic layer was separated, and the aqueous layer was extracted with methylene chloride (100 mL). The combined organic layer was dried over sodium sulfate, followed by filtration, and concentration under reduced pressure. The resulting residue was subjected to chromatography (ethyl acetate:n-hexane=1:10) to give the compound of formula (5a) (7.94 g, 93.3%).

$^1$H NMR (300 MHz, CDCl$_3$, δ ppm): 7.67-7.69 (m, 4H), 7.32-7.45 (m, 6H), 7.01 (d, J=8.7 Hz, 1H), 6.70 (d, J=3.0 Hz, 1H), 6.52 (dd, J=8.7 Hz, 1H), 5.14 (s, 1H), 4.82 (s, 1H), 4.72 (d, J=6.0 Hz, 1H), 4.26 (d, J=6.0 Hz, 1H), 3.51 (q, J=4.5 Hz, 1H), 2.79-2.92 (m, 2H), 2.46 (t, J=7.8 Hz, 1H), 1.73 (t, J=7.2 Hz, 1H), 1.55 (s, 3H), 1.20-1.30 (m, 15H), 1.10 (s, 9H), 0.86 (m, 12H)

Example 3: Synthesis of Compound of Formula (6a)

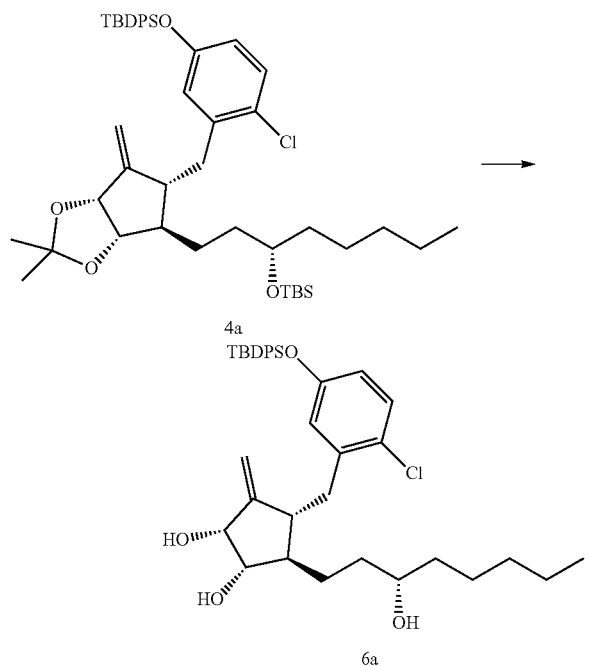

The compound of formula (5a) (7.9 g) was dissolved in THF (24 mL) and then cooled to 0° C. 90% trifluoroacetic acid (63.52 mL) was slowly added dropwise thereto. After warming the resulting solution to room temperature, 6N sodium hydroxide aqueous solution was added to adjust pH to 8-9. Ethyl acetate (200 mL) and water (100 mL) were added thereto, followed by stirring. Then, the organic layer was separated and dried over sodium sulfate, followed by filtration and concentration under reduced pressure. The resulting residue was subjected to chromatography (ethyl acetate:n-hexane=2:1) to give the compound of formula (6a) (5.52 g, 86.7%).

$^1$H NMR (300 MHz, CDCl$_3$, δ ppm): 7.68-7.71 (m, 4H), 7.35-7.46 (m, 6H), 7.05 (d, J=8.7 Hz, 1H), 6.58-6.61 (m, 2H), 5.12 (s, 1H), 4.74 (s, 1H), 4.21 (t, J=4.8 Hz, 1H), 3.64 (bs, 1H), 3.41 (bs, 1H), 2.84-2.91 (m, 1H), 2.55-2.62 (m, 1H), 2.46 (bs, 1H), 2.27-2.36 (m, 2H), 1.53-1.59 (m, 1H), 1.47 (bs, 1H), 1.23-1.32 (m, 9H), 1.09 (s, 9H), 0.88 (t, J=6.3 Hz, 3H).

Example 4: Synthesis of Compound of Formula (7a)

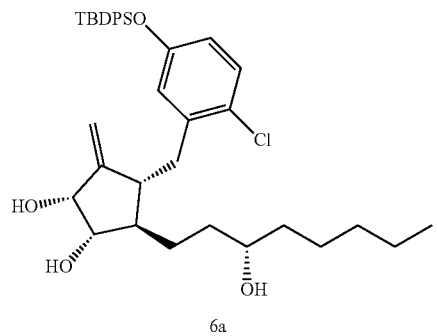

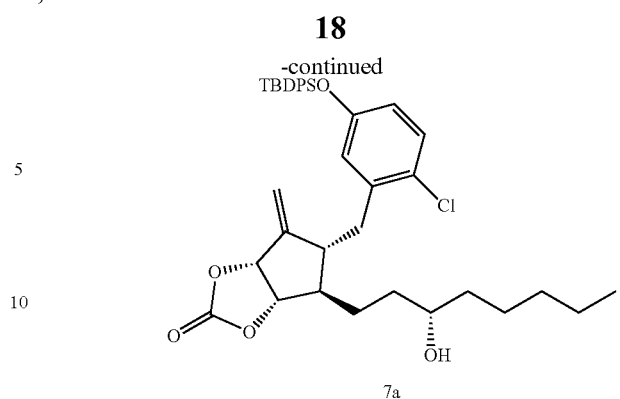

The compound of formula (6a) (242 mg) was dissolved in THF (3 mL), and CDI (127 mg) and DMAP (95 mg) were added thereto, followed by stirring at room temperature for an hour and 30 minutes. After the completion of the reaction was confirmed, saturated ammonium chloride aqueous solution (10 mL) and ethyl acetate (30 mL) were added and stirred. The organic layer was separated and dried over sodium sulfate, followed by filtration and concentration under reduced pressure. The resulting residue was subjected to chromatography (ethyl acetate:n-hexane=1:2.5) to give the compound of formula (7a) (162 mg, 64.3%).

$^1$H NMR (300 MHz, CDCl$_3$, δ ppm): 7.67-7.71 (m, 4H), 7.34-7.45 (m, 6H), 7.04 (d, J=8.4 Hz, 1H), 6.55-6.61 (m, 2H), 5.32 (s, 1H), 5.14 (d, J=5.1 Hz, 1H) 4.98 (s, 1H), 4.66 (dd, J=7.2 Hz, 1H), 3.42 (bs, 1H), 2.63-2.80 (m, 2H), 2.43-2.49 (m, 1H), 2.03 (s, 1H), 1.94-1.96 (m, 1H), 1.54 (s, 1H), 1.22-1.35 (m, 10H), 1.10 (s, 9H), 0.88 (t, J=6.6 Hz, 3H).

Example 5: Synthesis of Compound of Formula (5a)

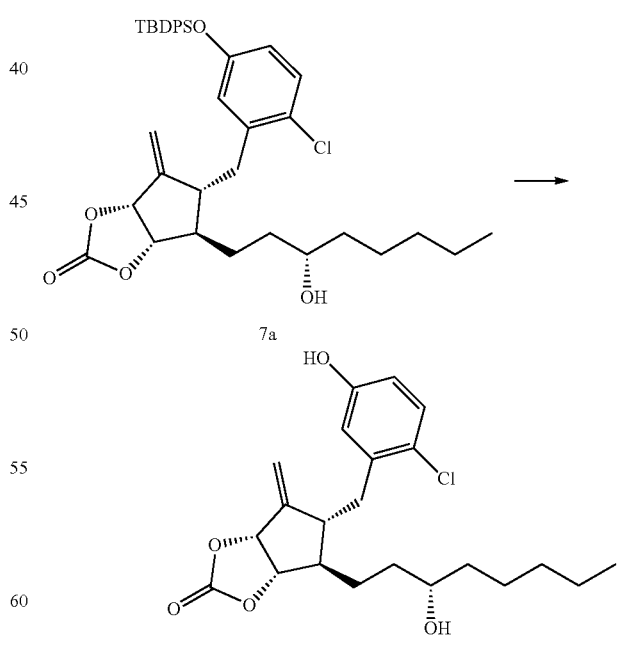

The compound of formula (7a) (95 mg) was dissolved in THF (3 mL), and cooled to 0° C. TBAF (47 mL) was added thereto, followed by additional stirring for 30 minutes. After the completion of the reaction was confirmed, saturated ammonium chloride aqueous solution (20 mL) and ethyl acetate (40 mL) were added, followed by additional stirring for 30 minutes. The organic layer was separated and dried over sodium sulfate, followed by filtration and concentration under reduced pressure. The resulting residue was subjected to chromatography (ethyl acetate:n-hexane=1:1) to give the compound of formula (8a) (60 mg, 97.9%).

$^1$H NMR (300 MHz, CDCl$_3$, δ ppm): 7.85 (s, 1H), 7.15 (d, J=8.4 Hz, 1H) 6.61-6.68 (m, 2H), 5.41 (s, 1H), 5.23 (d, J=7.2 Hz, 1H), 5.10 (s, 1H), 4.79 (d, J=6.9 Hz, 1H), 3.51 (bs, 1H), 2.79 (bs, 4H), 2.13 (bs, 1H), 2.05 (s, 1H), 1.23-1.37 (m, 10H), 0.87 (t, J=6.3 Hz, 3H).

Example 6: Synthesis of Compound of Formula (9a)

Example 7: Synthesis of Compound of Formula (10a)

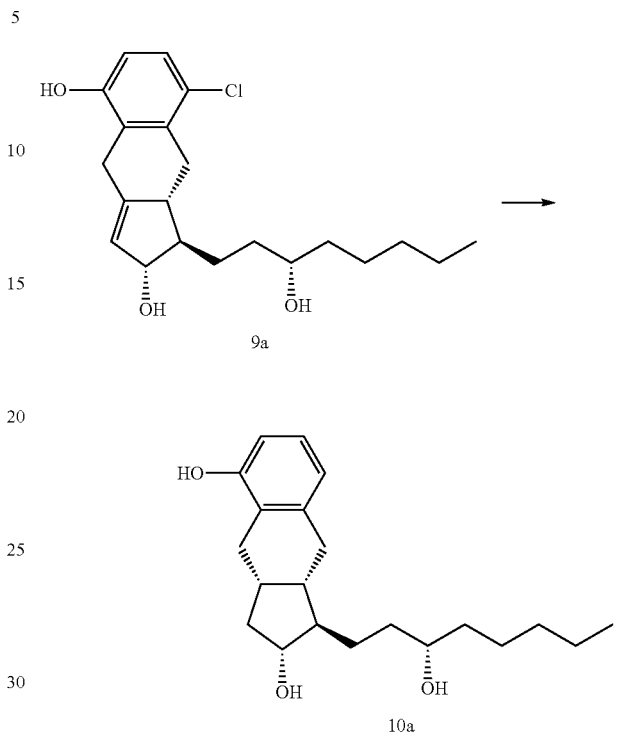

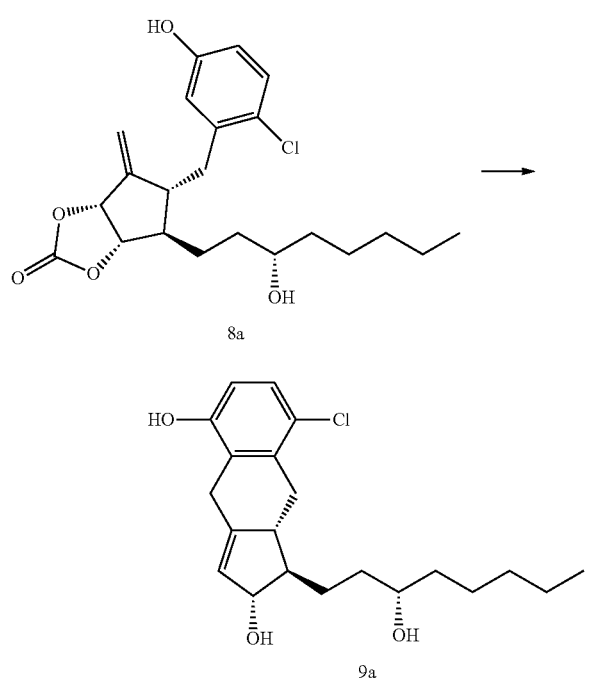

The compound of formula (8a) (60 mg) was dissolved in toluene (3.5 mL), and Pd(dba)$_2$ (4.48 mg) and PPh$_3$ (4.59 mg) were added thereto, followed by stirring at room temperature for an hour. After the completion of the reaction was confirmed, saturated ammonium chloride aqueous solution (10 mL) and ethyl acetate (30 mL) were added, followed by additional stirring. The organic layer was separated and dried over sodium sulfate, followed by filtration and concentration under reduced pressure. The resulting residue was subjected to chromatography (ethyl acetate:n-hexane=1:1) to give the compound of formula (9a) (34.7 mg, 64.7%).

$^1$H NMR (300 MHz, CDCl$_3$, δ ppm): 6.93 (d, J=8.7 Hz, 1H), 6.52 (d, J=8.7 Hz, 1H), 5.45 (s, 1H), 4.40 (s, 1H), 3.51 (m, 1H), 3.49 (s, 1H), 3.33-3.42 (m, 2H), 3.23-3.28 (m, 1H), 2.19-2.24 (m, 2H), 1.64-1.74 (m, 2H), 1.49-1.61 (m, 3H), 1.20-1.40 (m, 8H), 0.84 (t, J=6.6 Hz, 3H).

The compound of formula (9a) (34.7 mg) was dissolved in methanol (3 mL), and 10% Pd/C (9 mg) and triethylamine (10.7 mg) were added thereto, followed by stirring under hydrogen condition for 15 hours. After the completion of the reaction was confirmed, the resulting solution was filtered through a celite pad, and the filtrate was concentrated under reduced pressure. The resulting residue was subjected to chromatography (ethyl acetate:n-hexane=1:1) to give the compound of formula (10a) (20.5 mg, 65%).

$^1$H NMR (300 MHz. CDCl$_3$, δ ppm): 6.92 (t, J=7.5 Hz, 1H), 6.64 (d, J=7.8 Hz, 2H), 3.53-3.68 (m, 2H), 2.45-2.74 (m, 4H), 2.27-2.34 (m, 1H), 2.06-2.12 (m, 1H), 1.88-1.98 (m, 1H), 1.05-1.24 (m, 14H), 0.94 (t, J=6.6 Hz, 3H).

Example 8: Synthesis of Compound of Formula (12a)

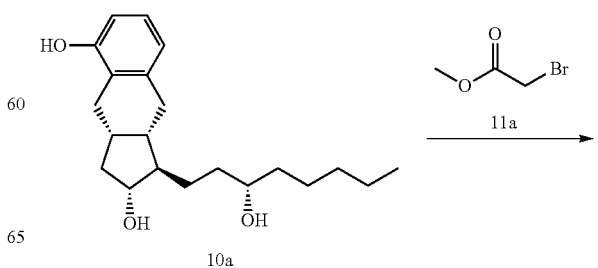

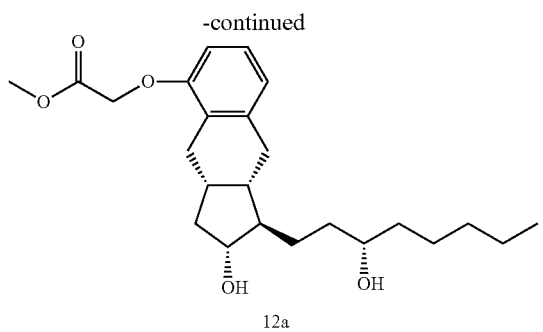

12a

To the compound of formula (10a) (440 mg) dissolved in acetone (4.0 mL) were added potassium carbonate (549 mg) and the compound of formula (11a) (405 mg). The resulting solution was stirred at 50-60° C. for 10-16 hours, and the completion of the reaction was confirmed by HPLC. The resulting solution was cooled to 15-25° C., filtered, and concentrated. Ethyl acetate (4.5 mL) and water (5.0 mL) were added and stirred. The organic layer was separated and dried over sodium sulfate (1.0 g), followed by filtration and concentration. The resulting residue was subjected to chromatography (ethyl acetate:n-hexane=1:1) to give the compound of formula (12a) (400 mg, 74.8%).

$^1$H NMR (300 MHz, CDCl$_3$, δ ppm): 7.07 (t, J=7.8, 1H), 6.81 (d, J=7.5 Hz, 1H), 6.63 (d, J=7.8 Hz, 1H), 4.63 (s, 2H), 3.79 (s, 3H), 3.54-3.76 (m, 2H), 2.88 (dd, J=14.7, 5.7 Hz, 1H), 2.76 (dd, J=14.1, 6.0 Hz, 1H), 2.42-2.59 (m, 2H), 2.14-2.30 (m, 2H), 1.85-1.94 (m, 1H), 1.12-1.75 (m, 14H), 0.90 (t, J=7.0 Hz, 3H).

$^{13}$C NMR (75 MHz, CDCl$_3$, δ ppm): 169.72, 154.89, 141.06, 127.81, 126.14, 121.63, 109.69, 76.60, 72.58, 66.00, 52.31, 52.16, 41.44, 41.28, 37.45, 35.00, 33.74, 32.79, 31.91, 28.66, 25.98, 25.38, 22.65, 14.06.

Example 9: Synthesis of Compound of Formula (1a)

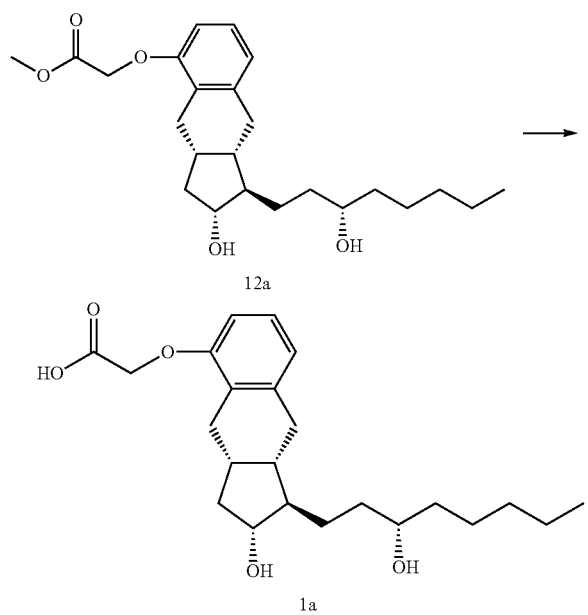

To the compound of formula (12a) (0.38 g) dissolved in ethanol (2.0 mL) was added sodium hydroxide (75 mg) dissolved in water (2.0 mL), followed by stirring for 3-5 hours. The completion of the reaction was confirmed by HPLC. After the reaction solvent was evaporated, water (2.0 mL) was added, followed by stirring. Hydrochloric acid (0.21 g) dissolved in water (1.82 mL) was added for acidification to pH 3-4. Ethyl acetate (4.5 mL) was added and stirred for 20-30 minutes, and the organic layer was separated. Water (5.0 mL) was added to the separated organic layer and stirred for 20-30 minutes, and then the organic layer was separated. Saline water (5.0 mL) was added to the separated organic layer, followed by stirring for 20-30 minutes. The organic layer was separated, and dried over sodium sulfate, followed by filtration and concentration to give the compound of formula (1a) (367 mg, 100%).

$^1$H NMR (300 MHz, MeOD, δ ppm): 7.05 (t, J=8.0 Hz, 1H), 6.79 (d, J=7.2 Hz, 1H), 6.70 (d, J=8.4 Hz, 1H), 4.62 (s, 2H), 3.52-3.67 (m, 2H), 2.61-2.80 (m, 3H), 2.50 (dd, J=14.4, 6.0 Hz, 1H), 2.21-2.34 (m, 1H), 1.86-2.12 (m, 2H), 1.05-1.76 (m, 14H), 0.92 (t, J=7.0 Hz, 3H).

$^{13}$C NMR (75 MHz, MeOD, δ ppm): 172.93, 156.52, 142.16, 128.69, 127.15, 122.42, 110.79, 77.61, 72.89, 66.56, 52.71, 498.83, 49.55, 49.26, 42.30, 42.01, 38.28, 36.04, 34.56, 34.06, 33.14, 29.60, 26.61, 26.48, 23.73, 14.41.

The invention claimed is:

1. A compound of the following formula (9):

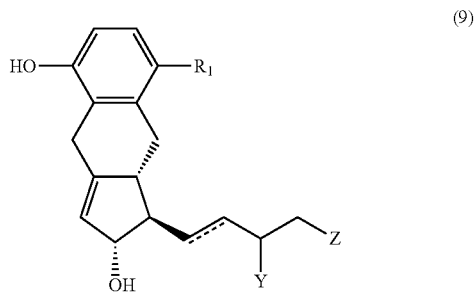

wherein, $\overline{\phantom{xx}}$ represents a single or double bond between carbon atoms, R$_1$ represents hydrogen or a halogen, Y represents α-OR$_5$:β-H or α-H:β-OR$_5$, R$_5$ represents hydrogen, and Z represents a C$_1$-C$_6$ alkyl group.

2. The compound of formula (9) according to claim 1, wherein $\overline{\phantom{xx}}$ represents a single bond between carbon atoms, R$_1$ represents chlorine, Y represents α-OR$_5$:β-H, R$_5$ represents hydrogen, and Z represents n-butyl.

3. A method for preparing a compound of the following formula (9), which comprises a step of subjecting a compound of the following formula (8) to intramolecular Friedel-Crafts allylic alkylation:

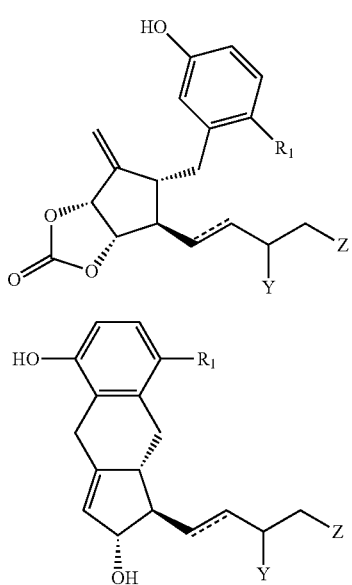

(8)

(9)

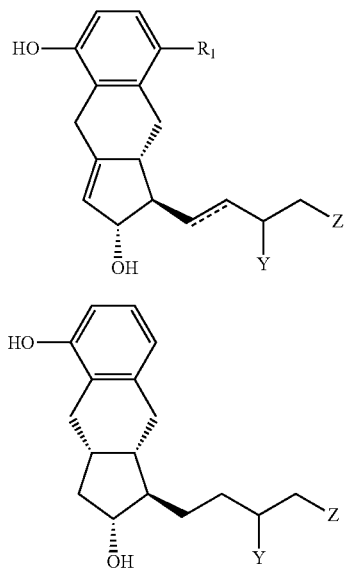

wherein,
⸺ represents a single or double bond between carbon atoms,
$R_1$ represents hydrogen or a halogen,
Y represents α-$OR_5$:β-H or α-H:β-$OR_5$,
$R_5$ represents hydrogen, and
Z represents a $C_1$-$C_6$ alkyl group.

4. A method for preparing a compound of the following formula (10), which comprises a step of subjecting a compound of the following formula (9) to hydrogenation:

(9)

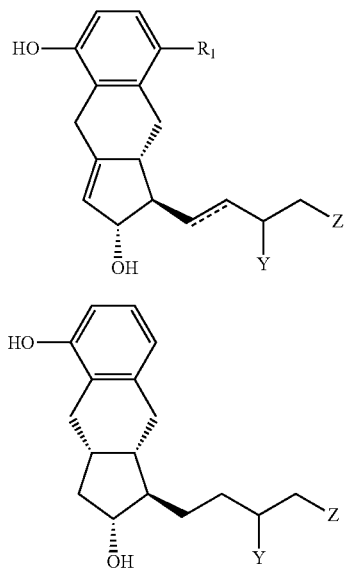

(10)

wherein,
⸺ represents a single or double bond between carbon atoms,
$R_1$ represents hydrogen or a halogen,
Y represents α-$OR_5$:β-H or α-H:β-$OR_5$,
$R_5$ represents hydrogen, and
Z represents a $C_1$-$C_6$ alkyl group.

5. The method according to claim 3, wherein the intramolecular Friedel-Crafts allylic alkylation is carried out using a palladium catalyst and a ligand.

6. The method according to claim 5, wherein the palladium catalyst is bis(dibenzylideneacetone)palladium(0), and the ligand is triphenylphosphine.

7. The method according to claim 4, wherein the hydrogenation is carried out using Pd/C under a basic condition.

8. A method for preparing a compound of the following formula (1), which comprises the steps of:

(vii) subjecting a compound of the following formula (9) to hydrogenation to obtain a compound of the following formula (10);

(viii) subjecting the compound of the following formula (10) to alkylation with a compound of the following formula (11) to obtain a compound of the following formula (12); and (ix) hydrolyzing an ester group of the compound of the following formula (12) to give the compound of formula (1):

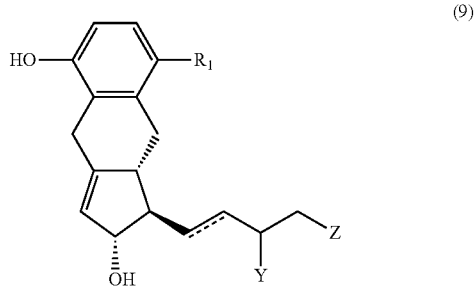

(9)

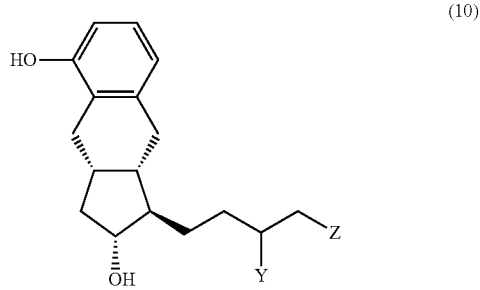

(10)

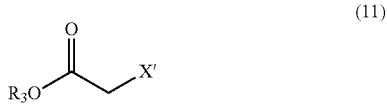

(11)

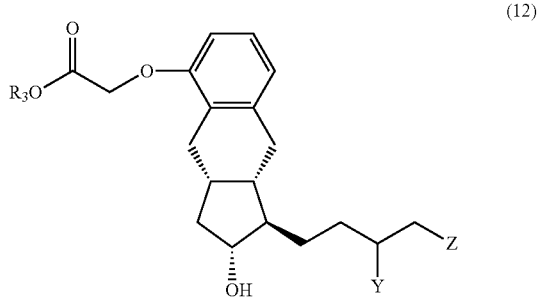

(12)

-continued
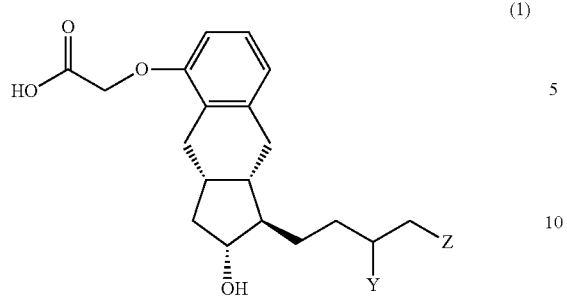
(1)
wherein,
⁓ represents a single or double bond between carbon atoms,
$R_1$ represents hydrogen or a halogen,
$R_3$ represents a $C_1$-$C_6$ alkyl group,
Y represents α-$OR_5$:β-H or α-H:β-$OR_5$,
$R_5$ represents hydrogen,
Z represents a $C_1$-$C_6$ alkyl group, and
X' represents a halogen.
\* \* \* \* \*